US012599512B2

(12) United States Patent
    Collins

(10) Patent No.:     US 12,599,512 B2
(45) Date of Patent:       Apr. 14, 2026

(54) FEMININE NAPKIN ASSEMBLY

(71) Applicant: Charity Collins, Los Angeles, CA (US)

(72) Inventor:  Charity Collins, Los Angeles, CA (US)

( * ) Notice:    Subject to any disclaimer, the term of this patent is extended or adjusted under 35 U.S.C. 154(b) by 168 days.

(21) Appl. No.: 17/591,936

(22) Filed:    Feb. 3, 2022

(65)            Prior Publication Data
        US 2023/0240910 A1      Aug. 3, 2023

(51) Int. Cl.
    *A61F 13/505*       (2006.01)
    *A61F 13/15*        (2006.01)
    *A61F 13/537*       (2006.01)
(52) U.S. Cl.
    CPC ...... *A61F 13/505* (2013.01); *A61F 13/15203* (2013.01); *A61F 13/537* (2013.01); *A61F 2013/16* (2013.01); *A61F 2013/53765* (2013.01)
(58) Field of Classification Search
    CPC .............. A61F 13/505; A61F 13/15203; A61F 13/537; A61F 2013/16; A61F 2013/53765; A61F 13/47254; A61F 2013/47281; A61F 2013/4729; A61F 2013/49098; A61F 2013/4951; A61F 2013/51383; A61F 13/491; A61F 13/51104; A61F 13/532
    See application file for complete search history.

(56)            References Cited
        U.S. PATENT DOCUMENTS 4,533,357  A  *  8/1985  Hall ...................... A61F 13/472
                                                       604/401
2008/0172019  A1*  7/2008  Chien ............... A61F 13/47218
                                                       604/385.04
2009/0312729  A1*  12/2009  Roche del Ayala ........................
                                                       A61F 13/5605
                                                       604/385.01
2013/0237940  A1*  9/2013  Wang ................ A61F 13/49004
                                                       604/377
2018/0064585  A1*  3/2018  Park .................. A61F 13/47272

* cited by examiner

*Primary Examiner* — Rebecca E Eisenberg
*Assistant Examiner* — Gabriella E Burnette
(74) *Attorney, Agent, or Firm* — Cohen IP law Group PC; Michael N. Cohen

(57)            ABSTRACT

A feminine napkin assembly including a menstrual pad coupled with a fluid guide that directs the flow of menstrual fluid to a desired location on the pad is provided. The fluid guide may include an elongate member with a proximal end coupled to an upper surface on the menstrual pad and a distal end extending forward towards the front end of the menstrual pad. The distal end of the elongate member may be placed against or inside the user's vagina. In this way, the fluid guide member may guide menstrual fluid to the desired location on the pad, thereby minimizing leakage of the fluid out the sides, rear, or front of the pad.

11 Claims, 3 Drawing Sheets

FEMININE NAPKIN ASSEMBLY

FIELD OF THE INVENTION

This invention relates to feminine hygiene products, including a sanitary napkin including an absorbent pad coupled with a menstrual fluid guide.

BACKGROUND

A wide variety of feminine products are available throughout the world for use by women during their menstrual cycles. The products aim to receive and contain the menstrual fluids released during the menstrual cycle in order to avoid soiling of the user's garments.

However, the products currently available for this purpose do not completely alleviate leakage, and the use of such products often results in stained garments.

Accordingly, there is a need for a feminine napkin assembly that guides the released menstrual fluid to a desired location on the napkin to maximize absorption of the fluid and to minimize leakage.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF EXEMPLARY EMBODIMENTS

In general, the feminine napkin assembly according to exemplary embodiments hereof includes a menstrual pad coupled with a fluid guide that directs the flow of menstrual fluid to a desired location on the pad. In this way, leakage of the fluid out the sides, rear, or front of the pad may be minimized.

Figure 1:
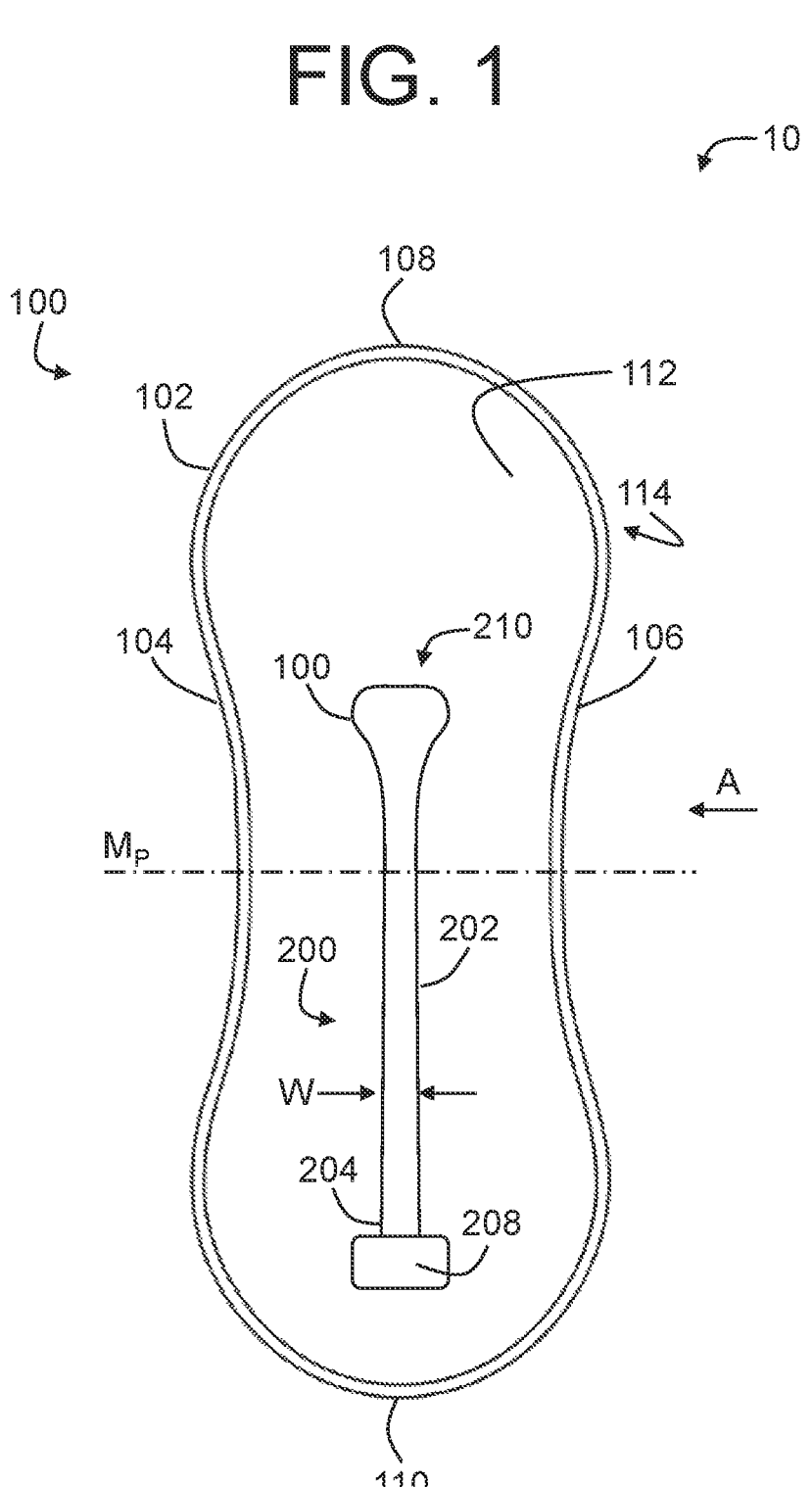
FIG. 1 shows a top view of a feminine napkin assembly according to exemplary embodiments hereof.
Figure 2:
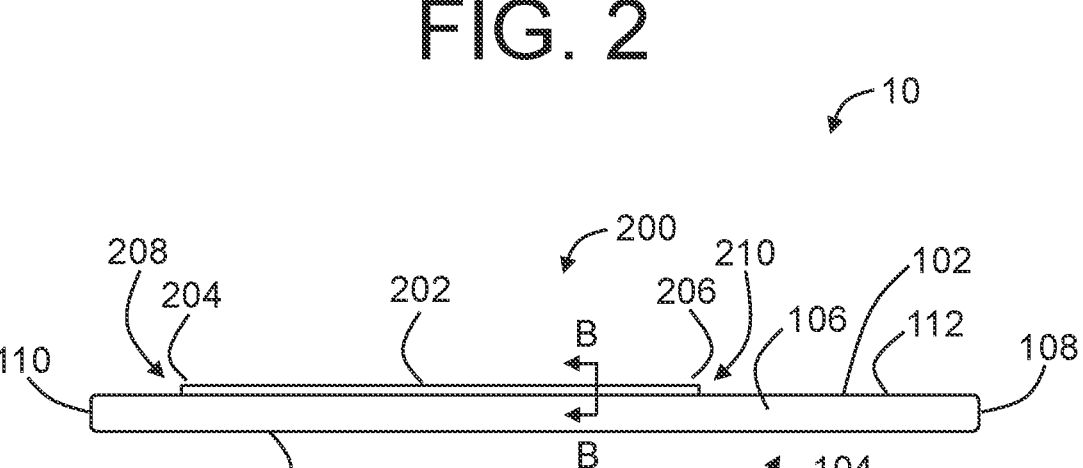
FIG. 2 shows side view of a feminine napkin assembly according to exemplary embodiments hereof.

In one exemplary embodiment hereof, as shown in FIGS. 1-2, the feminine napkin assembly 10 (also referred to herein as simply the assembly 10) includes a pad assembly 100 and a fluid guide assembly 200. FIG. 1 shows a top view of the feminine napkin assembly 10, and FIG. 2 shows the side view of the same taken from the perspective of the arrow A of FIG. 1. In general, the pad assembly 100 provides an absorbent napkin for use in absorbing menstrual fluid, and the fluid guide assembly 200 guides the menstrual fluid from the user's vagina to a specific location on the pad assembly 100. In this way, the menstrual fluid is directed onto a desired location of the pad assembly 100 where it may be properly absorbed thereby eliminating fluid leakage from the overall napkin assembly 10. The feminine napkin assembly 10 also may include other elements as necessary to fulfill its functionalities as described herein.

Pad Assembly 100

In some embodiments as shown in FIGS. 1-2, the pad assembly 100 includes a base 102 including a left side 104, a right side 106, a front side 108, a back side 110, a top side 112, and a bottom side 114. FIG. 1 shows the pad assembly 100 from the top and FIG. 2 shows the pad assembly 100 from the side (from the perspective of the arrow A of FIG. 1). The base 102 preferably comprises one or more types of absorbent material(s) adapted to absorb blood or other types of fluids that may be released from the user's vagina during menstruation, bleeding after giving birth, recovering from gynecologic surgery, or for other reasons.

The base 102 may be shaped in any way as is known in the art and may include a generally rectangular body with a rounded front side 108, a rounded back side 110, and with a width in the middle (between the front side 108 and the back side 110) that is less than the width toward either the front side 108 and/or the back side 110. However, it is understood that the base 102 may be shaped as any shape or form to perform its functionalities as described herein. In some embodiments, the base 102 may include "wings" or tabs that extend from the left side 104 and/or the right side 106 that wrap around the sides of underwear to add additional leak protection and help secure the pad assembly 100 in place.

In some embodiments, the pad assembly 100 may be disposable (e.g., single use) while in other embodiments the pad assembly 100 may be reusable (e.g., washable, and multi-use).

In some embodiments, disposable pad assemblies 100 may include a multilayered base 102. For example, the base 102 may include an absorbent core material comprising cotton (preferably 100% organic cotton), bleached rayon (cellulose made from wood pulp), other types of absorbent materials, and/or any combinations thereof. The absorbent layer may be disposed between a top-sheet on the top side 112 of the base 102 and a back-sheet on the bottom side 114 of the base 102. In some embodiments, the top-sheet may include a liquid permeable sheet to provide structural support to the top side 112 while allowing fluid to pass from the top side 112 to the absorbent core, and the back-sheet may include a liquid impermeable sheet with bottom facing adhesive for attaching the base 102 to an undergarment.

In some embodiments, reusable pad assemblies 100 may include a base 102 comprising cotton (e.g., cotton flannel), bamboo, hemp, other types of absorbent washable materials, and/or any combinations thereof.

It is understood that the pad assembly 100 may be formed as any size and thickness as known in the art, such as, without limitation, panty liner, ultra-thin, regular, maxi/super, overnight, maternity, and/or as other sizes and/or thicknesses.

Fluid Guide Assembly 200

Figure 3:
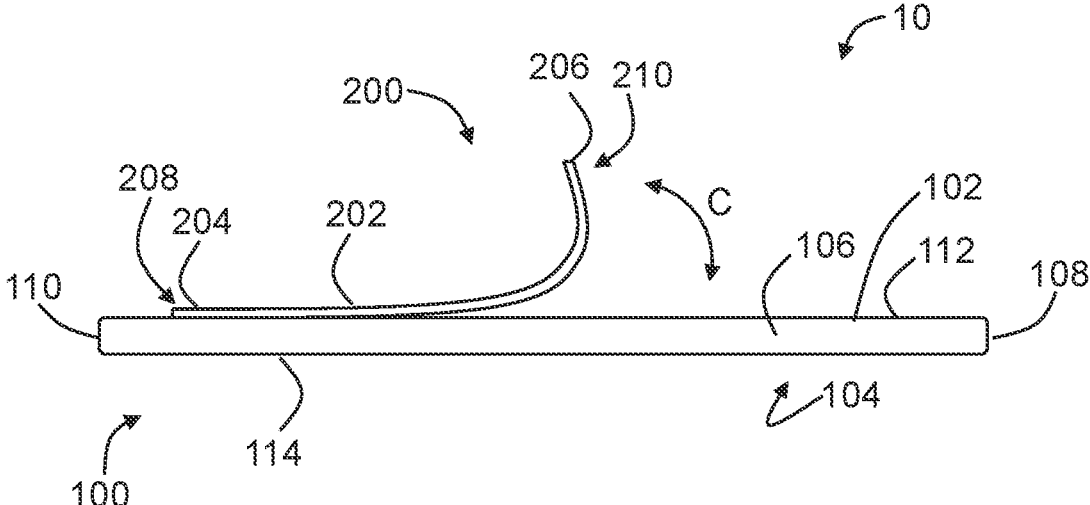
FIG. 3 shows aspects of a feminine napkin assembly according to exemplary embodiments hereof.

In some embodiments as shown in FIGS. 1-3, the fluid guide assembly 200 incudes an elongate member 202 with a proximal end 204 and a distal end 206. The proximal end 204 of the elongate member 202 is preferably attached to the top side 112 of the base 102 at an attachment location 208, e.g., between the base's 102's back side 110 and the base's 102's front side 108. In some embodiments, the distal end 206 of the elongate member 202 preferably extends from the attachment location 208 towards the front side 108 of the base 102.

The elongate member 202 preferably comprises an absorbent material such as cotton, rayon, and/or other types of suitable absorbent materials. The elongate member 202 may include a cross-section (taken from the perspective of cut-lines B-B of FIG. 2A) formed as a circle, an oval, a square, a rectangle, a trapezoid, other shaped cross-sections, and any combinations thereof. In some embodiments as described in other sections, the cross-section of the elongate member 202 may vary from its proximal end 204 to its distal end 206.

In some embodiments, the elongate member 202 may be spun from twisted fibers (e.g., as a string), woven, non-woven and/or knitted, braided, die-cut, pressed, compressed, extruded, molded, and/or formed using any suitable method.

In some embodiments as shown in FIG. 1, the attachment location 208 between the elongate member's proximal end 204 and the top side 112 of the base 102 is preferably located between the base's back side 110 and a midpoint $M_p$ between the base's back side 110 and the base's front side 108. However, it also is contemplated that the attachment location 208 may be generally located at the midpoint $M_p$ or between the midpoint $M_p$ and the base's front side 108 depending on the form and dimensions of the base 102. In some embodiments, the attachment location 208 is located closer to the base's back side 110 than to the midpoint $M_p$, while in other embodiments, the attachment location is located closer to the midpoint $M_p$ than to the base's back side 110. In some embodiments, the attachment location 208 is located about halfway between the midpoint $M_p$ and the base's back side 110. In some embodiments, the attachment location 208 is located about a quarter, a third, two thirds, or three quarters between the midpoint $M_p$ and the base's back side 110. It is understood that the attachment location 208 may be located at any location on the top side 112 of the base 102 as required for the elongate member 202 to perform its desired functionalities.

In some embodiments, the proximal end 204 of the elongate member 202 is attached to the top side 112 of the base 102 at the attachment location 208 using stitching, adhesive, fabric welding, other attachment methods, and/or any combinations thereof. In some embodiments, the elongate member 202 is integrally formed with the base 102 so that the base 102 and the elongate member 202 are formed together during the manufacturing process. In this embodiment, the elongate member 202 may comprise the same material as the base 102, while in other embodiments, the elongate member 202 may be formed using a different material than the material used to form the base 102.

In some embodiments as shown in FIG. 3, the elongate member 202 may include a tip member 210 at its distal end 206. The tip member 210 may be integrally formed with the elongate member 202 (e.g., using the same material during manufacturing), or may be formed separately and subsequently coupled to the elongate member's distal end 206.

In some embodiments, the tip member 210 may include a bulb or other type of member shaped (from a perspective from above and/or from the side) as a triangle, a trapezoid, a circle, an oval, an egg shape, a square, a rectangle, any other suitable shape, and/or any combinations thereof.

In some embodiments as shown in FIG. 1, the width W of the elongate member 202 may be generally linear from its proximal end 204 to its distal end 206 (e.g., to the tip member 210), may flare from its proximal end 204 to its distal end 206, may include curvatures and/or changes in its curvatures between its proximal end 204 and its distal end 206, or may otherwise vary in its size, shape, and/or form between its proximal end 204 and its distal end 206 as required for the elongate member 202 to perform its functionalities as described herein.

In some embodiments, the fluid guide assembly 200 is detachable from the pad assembly 100 so that the fluid guide assembly 200 may be replaced after use. In this case, after use, the used pad assembly 100 may be reusable (e.g., washable) and the used fluid guide assembly 200 may be removed from the pad assembly 100 and replaced with a new fluid guide assembly 200. The fluid guide assembly 200 may be releasably attached to the pad assembly 100 using an attachment mechanism 209 (see FIG. 4) including loop and hook material, one or more buttons, one or more snaps, one or more hooks, may be held within a slot in the pad assembly 100, and/or by other suitable attachment methods.

In some embodiments, the length of the elongate member 202 (from its proximal end 204 to its distal end 206) may be about 2"-8", or preferably about 3"-6", or more preferably about 4". In some embodiments, the width W of the elongate member 202 may be about 0.1"-1", or preferably about 0.25"-0.5", or more preferably about 0.35". It is understood that the elongate member 202 may be designed using any dimensions as necessary to enable the elongate member 202 to perform its functionalities as described herein.

In Use

In some embodiments as shown in FIG. 3, because the proximal end 204 of the elongate member 202 is attached to the top side 212 of the base 102 and the distal end 206 of the elongate member 202 is free (not attached to the base 102), the elongate member's distal end 206 (including the tip member 210) and at least a portion of the elongate member's body (between its proximal end 204 and its distal end 206) may be extended upward from the top side 112 of the base 102 in a direction represented by the arrow C.

When in use, the base 102 is placed in an undergarment with the base's back side 114 pressed against the material of the undergarment (and preferably held in place by the back side's 114's adhesive). The distal end 206 of the elongate member 202 (including the tip member 210 if present) is then placed against or inside the user's vagina. In this way, the guide member assembly 200 generally extends from the user's buttocks region (where it is attached to the base's top side 112 at the attachment location 208) forward to press against, or more preferably enter into, the user's vagina. For example, the tip member 210 may be inserted into the user's vagina to generally hold the elongate member 202 in place.

Figure 4:
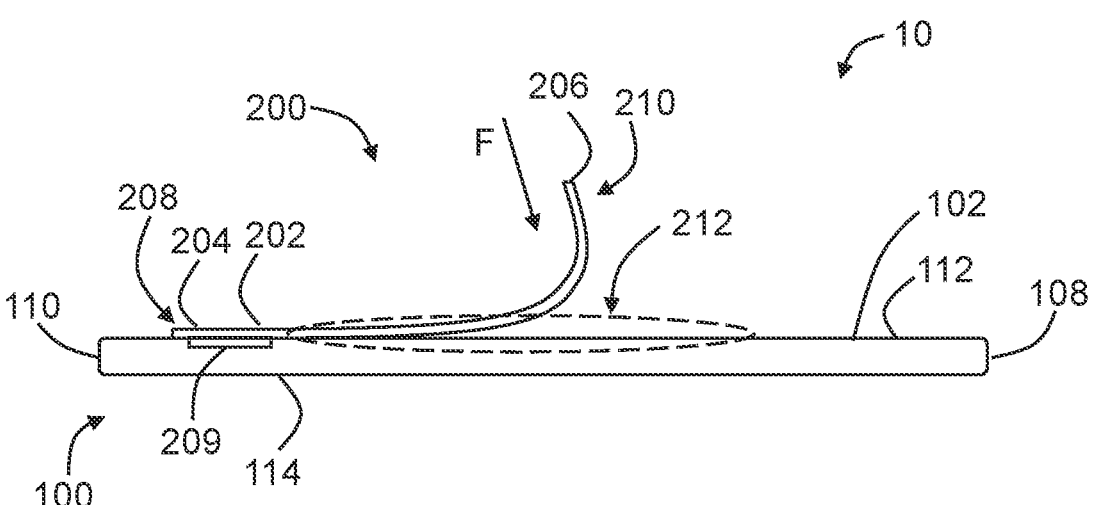
FIG. 4 shows aspects of a feminine napkin assembly according to exemplary embodiments hereof.

When in this configuration as shown in FIG. 4, fluid (e.g., menstrual fluid) that may be released from the user's vagina may generally adhere to and partially absorb into the elongate member 202 as it flows out of the vagina in the direction generally represented by the arrow F. As the fluid moves down the elongate member 202, the elongate member 202 acts as a guide to position the flow of the fluid onto a desired target area 212 on the top side 112 of the base 102. The target location on the top side 112 preferably includes an optimal absorbent location (e.g., of cotton material) so that the fluid may be properly absorbed by the base 102. The target area 212 may include any area on the top side 112 of the base 102, especially in the area between the elongate member 202 and the front side 108 of the base 102 and where the elongate member 202 may intersect or otherwise come into contact with the base's top side 112. In some embodiments, the target area 212 may include extra absorbent material to accommodate the flow of fluid to this area 212. Because the fluid is guided to the target area 212 by the guide assembly 200, potential spillage of the fluid (e.g., out the left, right, front, or back sides 104, 106, 108, 110 of the base 102) may be minimized.

It is understood that the steps described above are meant for demonstration and that additional steps may be performed, not all of the described steps may be performed, and the steps may be taken in different orders. It also is understood that the scope of the assembly 10 is not limited in any way by the steps taken during its use.

It also is understood that any aspect and/or element of any embodiment of the assembly 10 described herein or otherwise may be combined with any other aspect and/or element of any other embodiment described herein or otherwise in any way to form additional embodiments of the assembly 10 all of which are within the scope of the assembly 10.

Where a process is described herein, those of ordinary skill in the art will appreciate that the process may operate without any user intervention. In another embodiment, the process includes some human intervention (e.g., a step is performed by or with the assistance of a human).

As used herein, including in the claims, the phrase "at least some" means "one or more," and includes the case of only one. Thus, e.g., the phrase "at least some ABCs" means "one or more ABCs", and includes the case of only one ABC.

As used herein, including in the claims, term "at least one" should be understood as meaning "one or more", and therefore includes both embodiments that include one or multiple components. Furthermore, dependent claims that refer to independent claims that describe features with "at least one" have the same meaning, both when the feature is referred to as "the" and "the at least one".

As used in this description, the term "portion" means some or all. So, for example, "A portion of X" may include some of "X" or all of "X". In the context of a conversation, the term "portion" means some or all of the conversation.

As used herein, including in the claims, the phrase "using" means "using at least," and is not exclusive. Thus, e.g., the phrase "using X" means "using at least X." Unless specifically stated by use of the word "only", the phrase "using X" does not mean "using only X."

As used herein, including in the claims, the phrase "based on" means "based in part on" or "based, at least in part, on," and is not exclusive. Thus, e.g., the phrase "based on factor X" means "based in part on factor X" or "based, at least in part, on factor X." Unless specifically stated by use of the word "only", the phrase "based on X" does not mean "based only on X."

In general, as used herein, including in the claims, unless the word "only" is specifically used in a phrase, it should not be read into that phrase.

As used herein, including in the claims, the phrase "distinct" means "at least partially distinct." Unless specifically stated, distinct does not mean fully distinct. Thus, e.g., the phrase, "X is distinct from Y" means that "X is at least partially distinct from Y," and does not mean that "X is fully distinct from Y." Thus, as used herein, including in the claims, the phrase "X is distinct from Y" means that X differs from Y in at least some way.

It should be appreciated that the words "first," "second," and so on, in the description and claims, are used to distinguish or identify, and not to show a serial or numerical limitation. Similarly, letter labels (e.g., "(A)", "(B)", "(C)", and so on, or "(a)", "(b)", and so on) and/or numbers (e.g., "(i)", "(ii)", and so on) are used to assist in readability and to help distinguish and/or identify, and are not intended to be otherwise limiting or to impose or imply any serial or numerical limitations or orderings. Similarly, words such as "particular," "specific," "certain," and "given," in the description and claims, if used, are to distinguish or identify, and are not intended to be otherwise limiting.

As used herein, including in the claims, the terms "multiple" and "plurality" mean "two or more," and include the case of "two." Thus, e.g., the phrase "multiple ABCs," means "two or more ABCs," and includes "two ABCs."

Similarly, e.g., the phrase "multiple PQRs," means "two or more PQRs," and includes "two PQRs."

The present invention also covers the exact terms, features, values and ranges, etc. in case these terms, features, values and ranges etc. are used in conjunction with terms such as about, around, generally, substantially, essentially, at least etc. (i.e., "about 3" or "approximately 3" shall also cover exactly 3 or "substantially constant" shall also cover exactly constant).

As used herein, including in the claims, singular forms of terms are to be construed as also including the plural form and vice versa, unless the context indicates otherwise. Thus, it should be noted that as used herein, the singular forms "a," "an," and "the" include plural references unless the context clearly dictates otherwise.

Throughout the description and claims, the terms "comprise", "including", "having", and "contain" and their variations should be understood as meaning "including but not limited to", and are not intended to exclude other components unless specifically so stated.

It will be appreciated that variations to the embodiments of the invention can be made while still falling within the scope of the invention. Alternative features serving the same, equivalent or similar purpose can replace features disclosed in the specification, unless stated otherwise. Thus, unless stated otherwise, each feature disclosed represents one example of a generic series of equivalent or similar features.

The present invention also covers the exact terms, features, values and ranges, etc. in case these terms, features, values and ranges etc. are used in conjunction with terms such as about, around, generally, substantially, essentially, at least etc. (i.e., "about 3" shall also cover exactly 3 or "substantially constant" shall also cover exactly constant).

Use of exemplary language, such as "for instance", "such as", "for example" ("e.g.,") and the like, is merely intended to better illustrate the invention and does not indicate a limitation on the scope of the invention unless specifically so claimed.

While the invention has been described in connection with what is presently considered to be the most practical and preferred embodiments, it is to be understood that the invention is not to be limited to the disclosed embodiment, but on the contrary, is intended to cover various modifications and equivalent arrangements included within the spirit and scope of the appended claims.

The invention claimed is:

1. A feminine pad assembly comprising:

an absorbent pad including a front end adapted to engage a user's vagina and a back end generally opposite the front end and a pad body extending between the front end and the back end, the pad body including an upper surface; and an elongate member including a proximal end and a distal end and an elongate member body with a maximum width of about 1.0 inch and extending from the proximal end to the distal end, the elongate member at its proximal end in contact with and parallel to the upper surface and entirely unsecured from the absorbent pad, the elongate member configured such that the distal end can be located in a position corresponding to a point of contact between the user's vagina and the front end of the absorbent pad when the user wears the feminine pad assembly.

2. The feminine pad assembly of claim 1 further including an elongate member tip coupled to the distal end of the elongate member.

3. The feminine pad assembly of claim 2 wherein the shape of the elongate member tip is selected from a group including a triangle, a trapezoid, a circle, an egg shape, an oval, a square, and a rectangle.

4. The feminine pad assembly of claim 2 wherein the elongate member body includes a first width that flares between the proximal end and the distal end of the elongate member.

5. The feminine pad assembly of claim 1 wherein the elongate member includes an elongate member cross section with a shape selected from a group including a circle, an oval, a square, a rectangle, and a trapezoid.

6. The feminine pad assembly of claim 1 wherein the absorbent pad is disposable, the absorbent pad comprising at least one of cotton and rayon.

7. The feminine pad assembly of claim 1 wherein the absorbent pad is reusable, the absorbent pad comprising at least one of cotton, bamboo, and hemp.

8. The feminine pad assembly of claim 6 wherein the absorbent pad is reusable, and the elongate member is replaceable.

9. The feminine pad assembly of claim 1 wherein a length between the proximal end of the elongate member and the distal end of the elongate member is about 2" to 8".

10. The feminine pad assembly of claim 1 wherein a width of the elongate member body is about 0.1" to 1.0".

11. A feminine pad assembly comprising:

an absorbent pad including a front end adapted to engage a user's vagina and a back end generally opposite the front end and a pad body extending between the front end and the back end, the pad body including an upper surface; and an elongate member including a proximal end and a distal end and an elongate member body with a maximum width of about 1.0 inch and extending from the proximal end to the distal end, the elongate member at its proximal end directly overlaid and parallel to the upper surface and entirely unsecured from the absorbent pad, the elongate member configured such that the distal end can be located in a position corresponding to a point of contact between the user's vagina and the front end of the absorbent pad when the user wears the feminine pad assembly.

* * * * *